United States Patent [19]

Seidel et al.

[11] Patent Number: 5,846,738

[45] Date of Patent: Dec. 8, 1998

[54] SYNTHETIC STANDARD FOR IMMUNOASSAYS

[75] Inventors: Christoph Seidel, Weilheim; Peter Bialk, Eberfing; Herbert Von der Eltz, Weilheim, all of Germany

[73] Assignee: Boehringer Mannheim GmbH, Mannheim, Germany

[21] Appl. No.: 762,695

[22] Filed: Dec. 12, 1996

Related U.S. Application Data

[63] Continuation of Ser. No. 325,589, Oct. 19, 1994, abandoned.

[30] Foreign Application Priority Data

| Oct. 20, 1993 | [DE] | Germany | 43 35 798.9 |
| May 20, 1994 | [DE] | Germany | 44 17 735.6 |
| Jun. 15, 1994 | [DE] | Germany | 44 20 742.5 |

[51] Int. Cl.⁶ ............................................. G01N 33/53
[52] U.S. Cl. ......................... 435/7.1; 435/5; 435/13; 435/7.9; 435/7.92; 435/69.3; 435/961; 435/967; 435/973; 436/8; 436/517; 436/518; 436/536; 530/350; 530/324; 530/325; 530/326; 530/327; 530/328; 530/329; 530/806
[58] Field of Search .................... 424/185.1, 193.1; 435/7.1, 7.9, 7.92, 13, 5, 69.1, 69.3, 69.7, 961, 967, 973; 436/517, 518, 536, 8; 530/333, 350, 324–329, 806, 811, 813

[56] References Cited

U.S. PATENT DOCUMENTS

| 4,859,765 | 8/1989 | Nester, Jr. et al. | 530/333 |
| 4,886,663 | 12/1989 | Houghten | 424/88 |
| 4,939,094 | 7/1990 | Kuga et al. | 435/252.33 |
| 5,357,042 | 10/1994 | Matsueda et al. | 530/328 |
| 5,411,869 | 5/1995 | Itak et al. | 435/7.93 |
| 5,436,126 | 7/1995 | Wang | 435/5 |
| 5,639,854 | 6/1997 | Sia et al. | 530/324 |

FOREIGN PATENT DOCUMENTS

| 0 306 813 | 3/1989 | European Pat. Off. . |
| 0 394 819 | 10/1990 | European Pat. Off. . |
| 0 472 205 | 2/1992 | European Pat. Off. . |
| 3112334 | 10/1982 | Germany | 435/967 |
| 3200065 | 9/1991 | Japan | 436/8 |

OTHER PUBLICATIONS

Derwent Abstract of TOSOH Corp. 91–3000 11/41 JP403200065A, Sep. 1991.

FG Gabriel et al., "Peptide based enzyme immunoassays for detecting hepatitis C antibodies . . . " J. Clin. Pathol. 47(4):357–359, Apr. 1994.

H.S. Marsden et al., "Advantages of branched peptides in serodiagnosis," J. of Immunol. Methods 147:65–72, 1992.

L. Mesnard et al., "Molecular Cloning and developmental expression of human cardiac troponin T," FEBS Letters 328(1,2):139–144, Aug. 1993.

*Primary Examiner*—Carol A. Spiegel
*Attorney, Agent, or Firm*—Nikaido Marmelstein Murray & Oram LLP

[57] ABSTRACT

A conjugate of at least two binding sites that bind specifically to the analyte-specific binding region of the receptor that is used for detection in a test, wherein the binding sites are linked by at least one soluble carrier substance and the conjugate is a product of a synthetic or recombinant production, dissolved in an aqueous solution in an exactly known amount is particularly suitable as a stable calibrator in a test for the detection of an analyte.

19 Claims, 6 Drawing Sheets

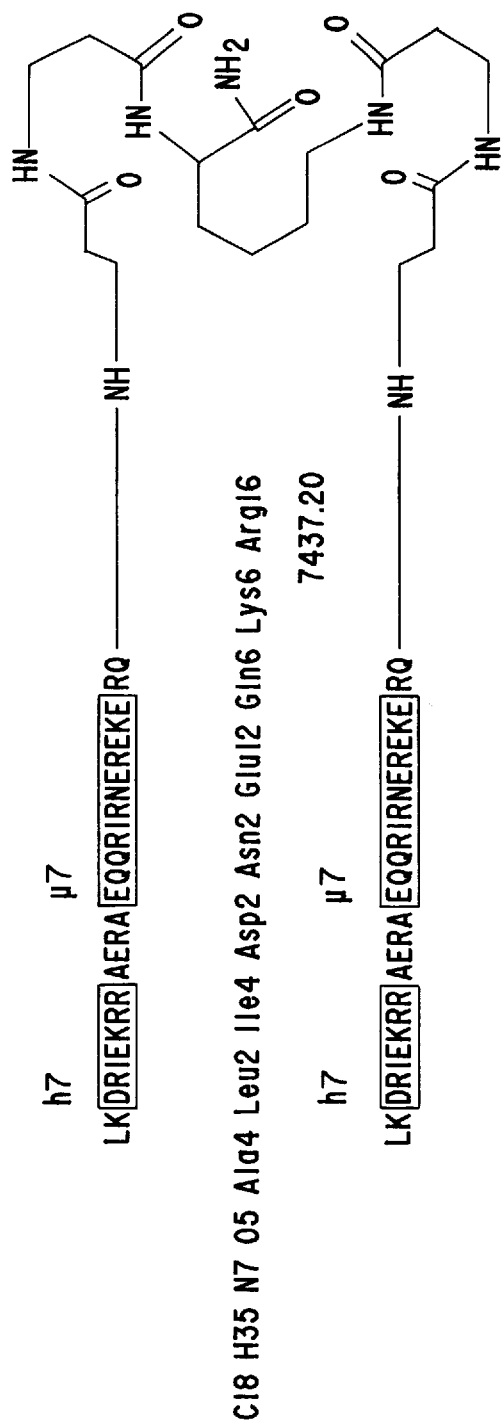

SYNTHETIC STANDARD FOR IMMUNOASSAYS

This application is a continuation of application Ser. No. 08/325,589 filed Oct. 19, 1994, now abandoned.

BACKGROUND OF THE INVENTION

1. Field of the Invention

The invention concerns a peptidic synthetic standard that can be used in immunoassays.

2. Description of Related Art

The analytes to be determined in immunology are often human proteins such as e.g. creatine kinase (e.g. CKMB), HCG, fibrin monomer, prolactin or troponin T. Human proteins isolated from natural sources are usually used to calibrate such tests. This isolation is difficult, expensive and requires the handling of human material that may be infectious. In this process it is also necessary to ensure that human proteins used for calibration contain no infectious contaminants. In addition the human proteins are not stable under all conditions. For example troponin T does not have an adequate long-term stability in solution as would be required for a liquid standard. In addition it is almost impossible to formulate a stable, common standard of such human proteins under the same buffer conditions since the stability maxima of the proteins are usually in different and, moreover, very narrow pH ranges.

SUMMARY OF THE INVENTION

The object of the invention is to provide standards for immunological methods of determination for the detection of human proteins via binding of the analyte to at least one analyte-specific receptor which are stable, and simple and cheap to produce, and which do not have the aforementioned disadvantages.

This object is achieved by a liquid stable calibrator for use in a test for the detection of an analyte comprising a conjugate of at least two binding sites that bind specifically to the analyte-specific binding region of the receptor that is used for detection in the test wherein the binding sites are connected by at least one soluble carrier substance and the conjugate is the product of a synthetic or recombinant production, dissolved in an aqueous solution in an exactly known amount.

The invention in addition concerns the use of this liquid stable calibrator to prepare a calibration curve in a test for the detection of an analyte.

The invention in addition concerns a method for the detection of an analyte in a sample by binding the analyte to at least one analyte-specific receptor and detecting the complex formed as a measure of the content of analyte in the sample which is characterized in that a) in a first step a known amount of a conjugate according to the invention is bound instead of the sample to the analyte-specific receptor,
b) the complex formed between conjugate and receptor is determined,
c) the result of the measurement from step b) is used to prepare a calibration curve,
d) the test for the analyte in the sample is carried out and the analyte concentration is determined by comparing the measured signal with the calibration curve obtained from c).

A calibration curve is to be understood as the relation of a plurality of measured values to analyte concentrations.

It has surprisingly turned out that such a conjugate is suitable in immunoassays as a synthetic standard and is stable over a long period in solution in wide pH ranges. Conjugates that are each comprised of only one binding site that binds specifically to the analyte-specific region of the receptor that is used for detection in the test are less suitable as standards in such tests and only have a low affinity for the receptors.

BRIEF DESCRIPTION OF THE DRAWINGS

FIGS. 2a and 2b show the peptides A (FIG. 2a) and B (FIG. 2b) used in example 3.

DESCRIPTION OF THE PREFERRED EMBODIMENTS

Figure 1:
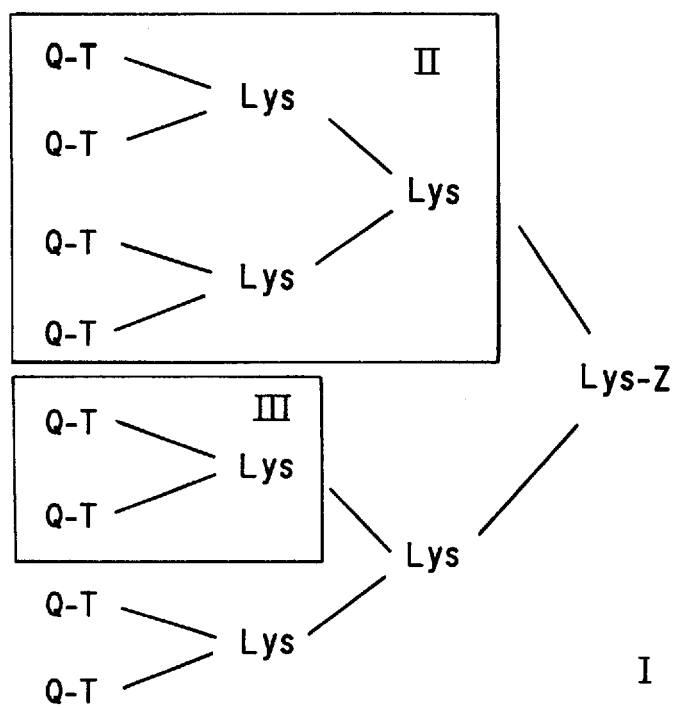
FIG. 1 shows a preferred tree-like structure of a conjugate of the invention. In this case II and III are also suitable substructures, T: spacer, optional; Q: antibody binding site (s).

Receptors are understood as all common molecules known to a person skilled in the art which bind to the analyte to be detected i.e. for example antibodies or binding proteins. Those receptors are particularly preferably used which have at least two analyte-specific binding regions i.e. for example antibodies or their bivalent fragments ($F(ab)_2$). The presence of two analyte-specific binding regions in the receptor enables a two-armed binding to the calibrator according to the invention in which at least two binding sites for the receptor are present per conjugate which is why, in comparison to a conjugate that only has one binding site, the binding constant is increased by the avidity of the receptor to the conjugate by 1000 to 10,000-fold.

Use of the calibrators according to the invention is also advantageous for monoclonal receptors such as Fab' fragments. These multivalent compounds enable the binding of a large number of labelled receptors which leads to a considerably increased signal. Solid-phase-bound monovalent receptors have properties comparable with solid-phase-bound multivalent receptors so that the peptide derivatives according to the invention are also advantageous for monovalent solid-phase-bound receptors.

A binding site is understood as a peptide whose sequence is part of the protein sequence of a protein antigen (analyte) and to which a receptor directed towards this protein specifically binds. Apart from these peptides, a binding site is also to be understood as peptides with amino acid sequences which have a specificity and/or affinity of binding to the receptor that is essentially equivalent to that of the aforementioned peptides. These peptides can preferably be derived from the aforementioned peptides by substitution, deletion or insertion of individual amino acid residues.

A binding site is also to be understood as peptide derivatives of the aforementioned peptides in which one or several amino acids have been derivatized by a chemical reaction. Examples of peptide derivatives according to the invention are in particular those molecules in which the backbone or/and reactive amino acid side groups, such as free amino groups, free carboxyl groups or/and free hydroxyl groups, have been derivatized. Specific examples of derivatives of amino groups are sulfonic acid amides or carboxylic acid amides, thiourethane derivatives and ammonium salts for example hydrochlorides. Examples of carboxyl group derivatives are salts, esters and amides. Examples of hydroxyl group derivatives are O-acyl or O-alkyl derivatives.

The term peptide derivative also encompasses those peptides in which one or several amino acids are substituted by naturally occurring or non-naturally occuring amino acid homologues of the 20 "standard" amino acids. Examples of such homologues are 4-hydroxyproline, 5-hydroxylysine, 3-methylhistidine, homoserine, ornithine, β-alanine and 4-aminobutyric acid. The peptide derivatives must have specificity or/and affinity of binding to the receptors that is essentially equivalent to that of the peptides from which they are derived.

A binding site is also to be understood as peptide-mimetic substances, denoted peptide-mimetics in the following, which have an essentially equivalent specificity or/and affinity of binding to the receptors as the aforementioned peptides or peptide derivatives. Peptide-mimetics are compounds that can substitute peptides with regard to their interaction with the receptor and can have an increased stability in particular towards proteinases or peptidases compared with the native peptides. Methods for the production of peptide-mimetics are described by Giannis and Kolter, "Angew. Chem." 105 (1993), 1303–1326 and Lee et al., Bull. Chem. Soc. Jpn. 66 (1993), 2006–2010.

The length of a receptor binding site is usually at least 4 amino acids. The length is preferably between 4 and 20, 4 and 15 or particularly preferably 4 and 10 amino acids. An analogous length or size of the molecule is required in the case of peptide-mimetics.

The following peptides are for example suitable as binding sites for the determination of troponin T:
SEQ ID NO. 1 Leu Lys Asp Arg Ile Glu Lys Arg Arg Ala Glu
SEQ ID NO. 2 Leu Ile Glu Ala His Phe Glu Asn
SEQ ID NO. 3 Leu Gln Ala Leu Ile Glu Ala His Phe Glu Asn
SEQ ID NO. 4 Leu Asn Glu Leu Gln Ala Leu Ile Glu Ala His Phe Glu Asn
SEQ ID NO. 5 Pro Pro Lys Ile Pro Asp Gly Glu Arg
SEQ ID NO. 6 Glu Gln Gln Arg Ile Arg Asn Glu Arg Glu Lys Glu
SEQ ID NO. 7 Ala Leu Ser Asn Met Met His Phe
SEQ ID NO. 8 Met Pro Asn Leu Val Pro Pro Lys Ile
SEQ ID NO. 9 Leu Gln Glu Lys Phe Lys Gln Gln Lys Tyr
SEQ ID NO. 10 Val Leu Arg Asn Arg Ile Asn Asp Asn Gln The peptides according to SEQ ID NO. 1, 2, 3, 4 and/or SEQ ID NO. 6 are particularly suitable. The entire DNA and amino acid sequence of troponin T is described in Mesnard, L. et al FEBS Letters 328, 1.2, (1993) 139–144.

The following peptides are for example suitable as binding sites for the determination of fibrin monomer:
SEQ ID NO. 11 Gly Pro Arg Val Val Glu Arg The conjugates according to the invention are particularly suitable as standards for the determination of troponin T, HCG and CKMB and fibrin monomer in immunological sandwich tests. Immunological sandwich tests for HCG, CKMB and fibrin monomer are described for example in:
J. F. O'Connor
Cancer Research 48, 1361–1366, (1988)

S. K. Gupta
Journal of immunological Methods 83 (1985) 159–168

B. Longhi
Journal of immunological Methods 92 (1986) 89–95

T. Chard
Human Reproduction vol 7 no 5 pp 701–710 (1992)

L. R. Witherspoon
Clin. Chem. 38/6 887–897 (1992)

Clin. Chem. 38/1, 144–147 (1992)

R. J. Norman
Ann. Clin. Biochem. (1990) 27:183–194

H. Christensen
Clin. Chem. 36/9, 1686–1688 (1990)

S. D. Figard
Eur. J. Clin. Chem. Clin. Biochem., 28, 1991, 77–80

U. Scheefers-Borchel
Proc. Nat. Acad. Sci USA 82 (1985) 7091–7095

H. Lill
Blood Coag. Fibrinol. 4 (1993) 97–102

C. E. Dempfle
Blood Coag. Fibrinol. 4 (1993) 79–86

Zabel, M.
Circulation (1993) 87 (5) p1542–50

Van Blerk, M.
Clin. Chem. 38, 12 (1992) pp2380–6

Buttery, J. E.
Clin. Biochem. 25,1 (1992) 11–13

A method for the determination of troponin T is described in EP-A-0 394 819.

It is possible to select binding sites for any desired protein analytes according to methods which are familiar to any person skilled in the art. Such methods are described for example in V. Regenmortel, Synthetic Polypeptides as Antigens, Elsevier 1988, 1–16.

The conjugate that is suitable in immunoassays as a synthetic standard contains at least two binding sites in each case which bind specifically to the analyte-specific binding region of the receptor that is used for detection in the test. In the case of a competitive assay in which only one analyte-specific receptor is necessary, the conjugate contains two identical or similar binding sites both of which bind to this receptor. In the case of an assay in which two analyte-specific receptors are necessary which are both capable of binding simultaneously to the analyte, such as a sandwich immunoassay, the conjugate in each case contains two identical or similar binding sites that are capable of binding to the two receptors. Two different receptors are usually used in these assays which do not compete for the same epitope of the analyte. In this case the conjugate thus contains two binding sites for the first and two binding sites for the second receptor. In some cases it is also possible to use identical receptors in these assays if for example the analyte contains repetitive epitopes or is composed of several identical subunits. In this case the conjugate contains at least four identical or similar binding sites which are capable of binding to the receptors.

The number of binding sites can, however, also be larger. If the conjugate contains a soluble polymer of high molecular weight as the carrier substance, up to 50 binding sites for each receptor binding region may be present. If the binding sites in the conjugate are coupled to the carrier substance to form a linear or branched synthetic oligomoer of amino acids and spacer molecules, then 2 to 16 is the preferred number of binding sites. In linear conjugates the carrier substance is preferably composed of a plurality of peptidic oligomers that are arranged between the binding sites. In such cases the carrier substance is preferably identical to the spacer. Branched conjugates preferably have a tree-like structure (cf. e.g. FIG. 1). The number of binding sites in such conjugates is preferably 2, 4, 8 or 16. In this case it is preferable that spacers are inserted between the ends of the carrier substance and the binding sites.

In a preferred embodiment of the conjugate the binding sites are covalently linked together via branching points with 2, 4 or 8 amino groups as the carrier substance. Such a branching point is a bifunctional or multifunctional molecule on the functionalities of which binding sites or, if necessary, further branching points can be bound. This binding can be direct or via a spacer. Preferred branching points are for example α, -bisamino acids such as lysine or α-bisamines. Such branched peptides are for example described in Tam, J. P. Proc. Natl. Acad. Sci. USA 85 (1988) 5409–5431, WO 92/18528 and Marsden, H. S. et al., J. Immunol. Meth. 147 (1992) 65–72.

The functionality of a branching site is understood as a chemical group that can bind to a chemical group in a binding site (if desired after prior activation). Examples of this are primary or secondary amino, carboxylic acid, sulfhydryl, alcohol, aldehyde and sulfonic acid functional groups.

Lysine and homooligomers of lysine preferably with 3 to 7 lysines are also preferred as the carrier substance for conjugates with a tree-like structure.

The binding sites which in each case are directed towards the same receptor can either have an identical or different amino acid sequence. However, it must be ensured that the binding sites specifically recognize the same binding region of the receptors.

It is expedient to link the binding sites together and/or covalently with the carrier substance via spacers of 3–40 atoms in length to form the conjugate. A spacer is understood as a bifunctional molecule that can bind to the ends of two binding sites or to one binding site and to the soluble carrier and as a result produces a spatial distance between these binding sites.

The spacers are preferably linear molecules with adequate polar properties for water solubility. The spacer is also particularly preferably composed of amino acid residues. These amino acids can correspond to the natural intermediate sequence of the binding sites in the natural analyte or be different from the natural sequence. In this case natural amino acids such as for example alanine, glycine, cysteine, lysine, aspartic acid, glutamic acid, serine, leucine or non-natural linear ω-amino acids such as e.g. β-alanine, γ-amino butyric acid or ω-aminocaproic acid are again preferred. They are coupled via covalent bonds (e.g. —CO—NH—, —NH—CO—, —S—S—, —CO—O—, —O—CO—) or via bivalent spacers. The spacer length must be chosen such that the receptors can bind substantially unhindered to the binding sites. A spacer length of over 40 atoms does not have any further particular advantages. In addition such molecules are more time-consuming to synthesize.

The spacers are preferably composed of 1–10 amino acids in each case. Preferred spacers are: oligoglycines, oligo-β-alanines, oligo-ω-aminocaproic acids or oligopeptides made of β-alamines and ω-aminocaproic acids.

The N-terminus of the conjugate can either be free or contain a bound organic residue such as e.g. an acetyl, tertiary butyloxycarboxyl, peptidyl, aryl or alkyl residue. The C-terminus can also be present in a free form as a carboxylate or amide or it can be derivatized with an organic residue and for example be an alkyl ester or an aryl ester.

In a preferred embodiment the C-terminus and N-terminus are linked via a bivalent spacer or a peptide sequence so that the molecule has a cyclic structure.

In a further embodiment the carrier substance can be a combination of spacer and branching points and represent a polymer which has a plurality of functional binding groups for the binding sites. Such polymers can for example be soluble polyamines, dextrans, polyacrylates, polymethacrylates, polypeptides, proteins or nucleic acids with a molecular weight of 1000 to 5 million Daltons, but preferably of 10,000 to 1 million Daltons. Soluble proteins such as albumins, immunoglobulins or β-galactosidase are particularly suitable as polymers. The polymers carry 2 to 500 groups capable of coupling. A large number of suitable methods for producing the bond between the binding sites and polymers is known to a person skilled in the art. It is expedient to activate the polymers in order to bind the binding sites to the polymers. The binding can for example be carried out via hetero of homobifunctional linkers or via the direct formation of an amide bond. It is particularly expedient to react a polymer carrying amino groups with a N-hydroxysuccinimide ester derivative of the binding site. The direct reaction of a polymer carrying SH groups with maleinimide derivatives of the binding site or the use of maleinimide-derivatized carrier polymers and binding sites carrying SH groups is particularly suitable.

The conjugates used according to the invention can be prepared according to known methods such as those described for example by J. P. Tam, Proc. Natl. Acad. Sci. USA, 58 (1988), 5409–5413; D. N. Pressmett et al., J. Biol. Chem. 263 (1988), 1719–1725; H. Lankinen, J. Gen. Virol. 70 (1989), 3159–3169; WO 92/18528 or H. S. Marsden, J. Immunol. Methods 147 (1992), 65–72.

The conjugates according to the invention comprising at least two binding sites and at least one soluble carrier substance are used as liquid calibrators to prepare a calibration curve in a test for the detection of an analyte. When preparing the liquid calibrators according to the invention one must take care that the conjugates are present in an exactly defined and known amount in the liquid calibrator. It is expedient to provide the liquid calibrators in various concentrations in order to prepare a calibration curve so that no further dilution steps are necessary before use. The concentration of the conjugate in the liquid calibrator depends on the analyte to be detected and usually covers the analyte concentrations that occur physiologically. Calibrator series are provided in typical concentrations of 0.1 to 1000 ng/ml. A liquid calibrator series for the troponin T test covers for example the conjugate concentrations of 0, 0.1, 0.5, 1, 5, 10, 50, 100 and 500 ng/ml. In the case of the fibrin monomer test the conjugate concentration in the calibrator series is for example 10, 50, 100, 250 and 500 ng/ml.

The term liquid stable calibrator means that after dissolving an exactly defined amount of the conjugate in a particular amount of a solvent, usually a buffer, the liquid calibrator which is thereby formed has a long stability. The dissolution of the conjugate in the solvent can already be carried out by the manufacturer. This has the advantage that the end user does not have to carry out any additional working steps. On the other hand the conjugate can also be dissolved by the user. The conjugate is provided by the manufacturer as a dry substance, for example as a lyophilisate. This has the advantage that an improper transport or an improper storage before use i.e. dissolution is less damaging.

The liquid calibrator contains further auxiliary substances such as for example buffers, stabilizers or preservatives in an exactly defined and known amount in addition to the conjugate. Sodium phosphate, MES or PIPES have proven to be particularly suitable as the buffer. The pH value is preferably 5.0–6.0. Bovine serum albumin can for example be used as the stabilizers. The calibrators according to the invention have a higher stability on storage than stabilizers that have been produced from the naturally occurring analytes. This effect is particularly pronounced when the analyte is a labile protein such as troponin T. The reasons for this can for example be proteolytic attack, unspecific binding to surfaces or a tendency to aggregate.

The invention in addition concerns a liquid stable universal calibrator for use in several tests for the detection of at least two different analytes.

The universal calibrator is composed of a mixture of at least two different aforementioned calibrators. Since these synthetic calibrators are exactly defined substances, their mutual influence in the mixture is very much smaller than with material from an organic source.

Methods for the detection of an analyte in a sample by binding the analyte to at least one analyte-specific receptor are familiar to a person skilled in the art and described for example in D. W. Chang, M. T. Perlstein, Immunoassay-a practical guide, Academic Press, Inc. (1987), Wisdom, Clin. Chem. 22/8 (1976), 1243–1255, Oellerich, J. Clin. Chem. Clin. Biochem. 18 (1980), 197–208 and Kage and Kottgen, mta 3 (1988), 10, 797–804.

The conjugates according to the invention can be used in homogeneous immunoassays as well as in heterogeneous immunoassays. Homogeneous assays are for example understood as a precipitation method such as TINIA (turbidimetric inhibition assay), an agglutination method, FPIA (fluorescence polarisation immunoassay) or CEDIA (cloned enzyme donor immunoassay) i.e. methods in which the degree of receptor-analyte reaction is quantified without separating the free and bound fractions. Heterogeneous assays are for example understood as radioimmunoassays or sandwich assays i.e. methods in which the degree of receptor-analyte reaction is quantified after separating the free from the bound fractions. Enzymatic label or fluorescent labels are for example used as the label in sandwich immunoassays. Such labels are known to a person skilled in the art and are described for example in:

D. L. Bates
Trends in Biotechnology 5 (7) (1987) pp204–209

M. A. Ator
JBC 262, 31, 14954–14960 (1987)

K. Beyzavi
Ann. Clin. Biochem. 24, 145–152 (1987)

J. Ennen
mta 4 (1989) 3, p. 199–203

J. Ennen
mta 4 (1989) 5, p. 414–416

Ekins, R.
J. Biolumin. Chemilumin., July 1989, 4 (1), p59–78

Helgert K.
Pharmazie Nov. 1989, 44 (11) p745–52

Ishikawa, E.
J. Clin. Lab. Anal. 1989, 3 (4) p252–65

Porstmann,
J. Immunol. Methods, June 24, 1992, 150 (1–2) p5–21

Ishikawa, E.
Mol. Cell Probes, April 1991, 5 (2) p 81–95

Weber, T. H.
Scand. J. Clin. Lab. Invest. Suppl., 1990, 201, p77–82

Walker, M. R.
Methods Biochem. Anal. 1992, 36, p179–208

King, W. J.
Immunol. Ser. 1990, 53, p 83–93

Ishikawa, E.
Clin. Chim. Acta, Dec. 17, 1990 194 (1), p51–72

The conjugates according to the invention have proven to be particularly suitable for use in sandwich assays. In this case the determination is carried out by incubating the sample with at least two analyte-specific receptors wherein one of these receptors is immobilized in a solid phase before or after the reaction with the analyte and the second receptor carries a label. After completion of the immunological reaction, the liquid phase and solid phase are separated and the label is determined in one of the two phases as a measure of the amount of analyte.

In the method for the detection of an analyte in a sample by binding the analyte to at least one analyte-specific receptor and detecting the complex formed as a measure of the content of the analyte in the sample, in a first step a known amount of the conjugate according to the invention is bound instead of the sample to the analyte-specific receptor. After determination of the complex formed between conjugate and receptor, a calibration curve is prepared from these results. Afterwards the analyte test is carried out and the analyte concentration is determined by comparing the measured signal with the calibration curve.

The conjugate according to the invention must have a particular composition depending on the method. If a method of detection is used in which only one analyte-specific receptor is necessary i.e. for example a competitive method, then a conjugate of at least two binding sites linked by at least one soluble carrier substance is used.

If a method of detection is used in which at least two analyte-specific receptors are necessary, such as a sandwich immunoassay, then a conjugate of at least two binding sites for each of these two receptors linked by at least one soluble carrier substance is used. The two receptors can either be identical i.e. recognize the same epitopes of the antigen or they can be different i.e. recognize different epitopes of the antigen. In the former case the antigen must have several identical epitopes which is for example the case for antigens with repetitive epitopes or identical subunits. An example of this is fibrin monomer. In this case the conjugate must therefore have at least four identical binding sites. In the second case the conjugate contains at least two binding sites for the first receptor and at least two binding sites for the second different receptor. Troponin T can for example be detected in this manner.

The invention is elucidated further by the following examples, figures and the sequence protocol.

FIG. 1 shows a preferred tree-like structure of a conjugate suitable according to the invention. In this case II and III are also suitable substructures, T: spacer, optional; Q: antibody binding site(s).

Figure 2B:
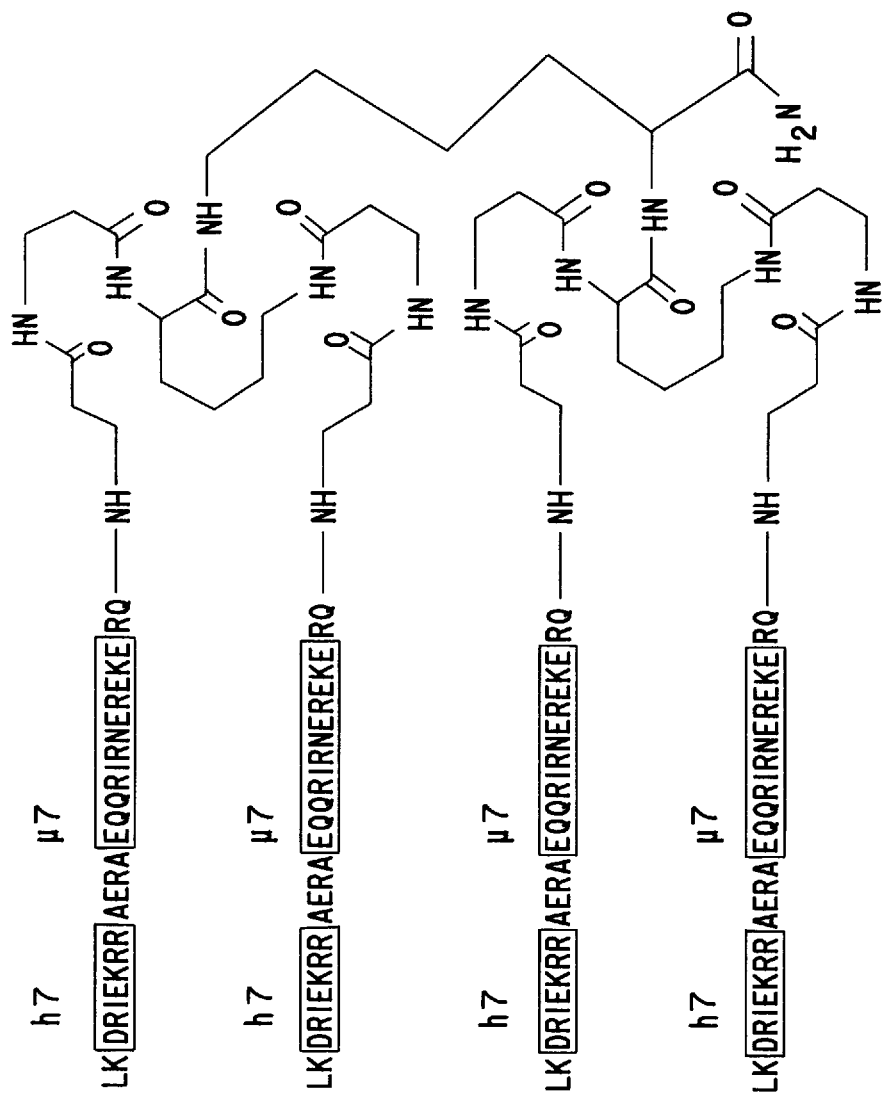

FIGS. 2a and 2b show the peptides A (FIG. 2a) and B (FIG. 2b) used in example 3.

Figure 3A:
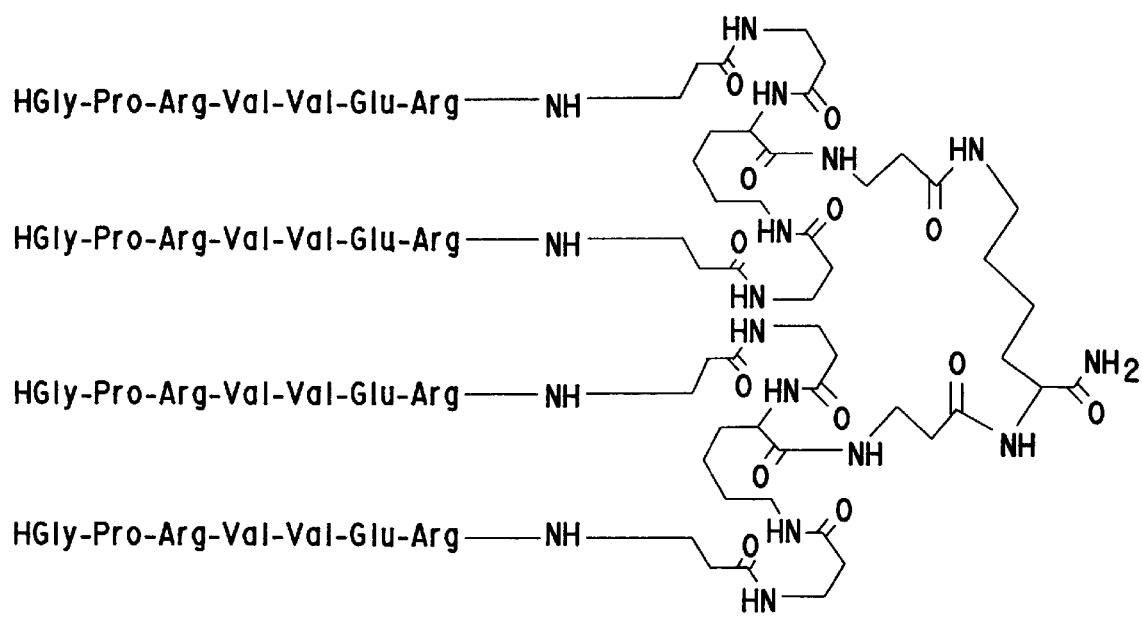
FIGS. 3a and 3b show the conjugates synthesized in example 8 (FIG. 3a) and 9 (FIG. 3b).
Figure 3B:
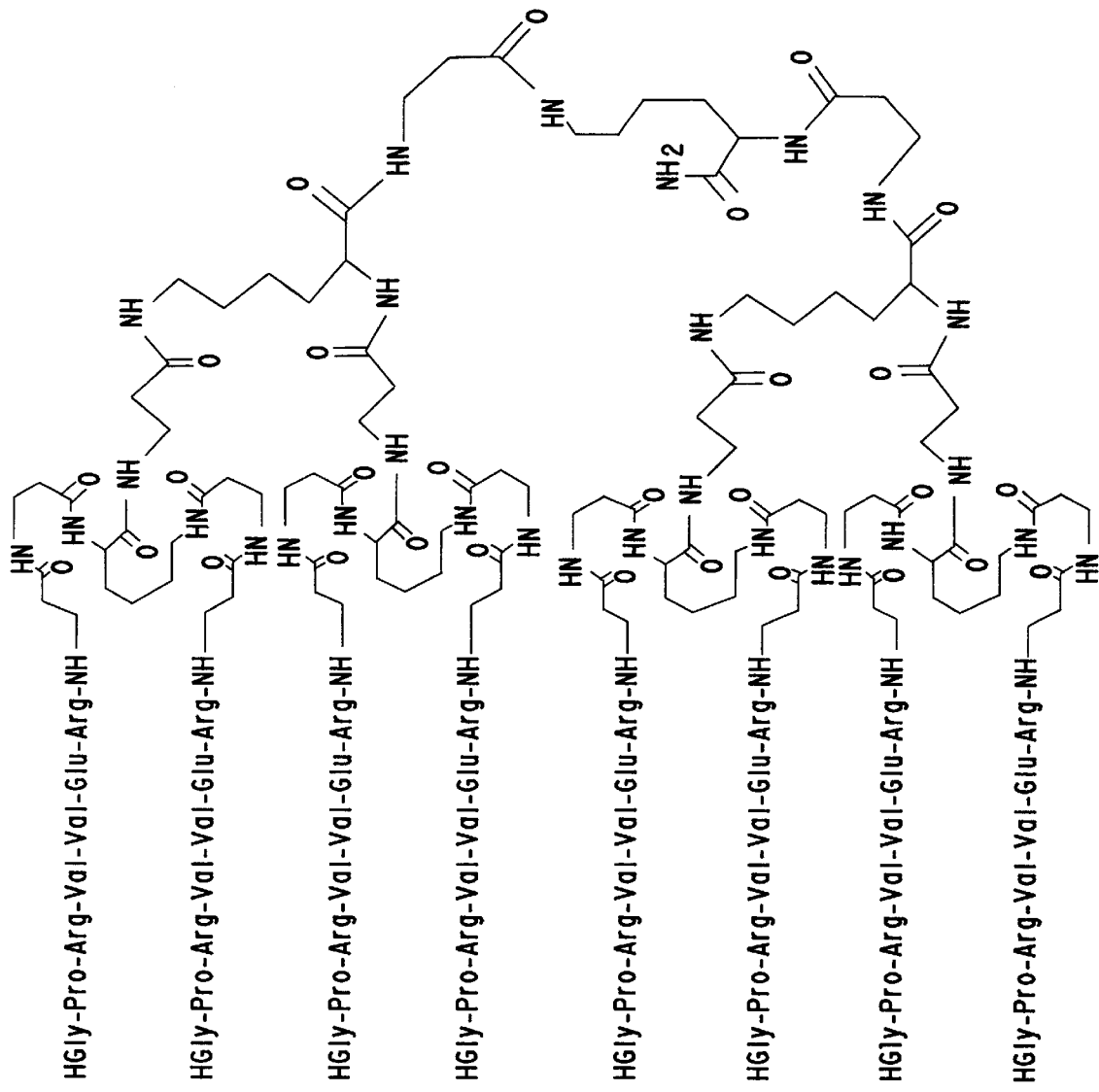

FIGS. 3a and 3b show the conjugates synthesized in example 8 (FIG. 3a) and 9 (FIG. 3b).

Figure 4:
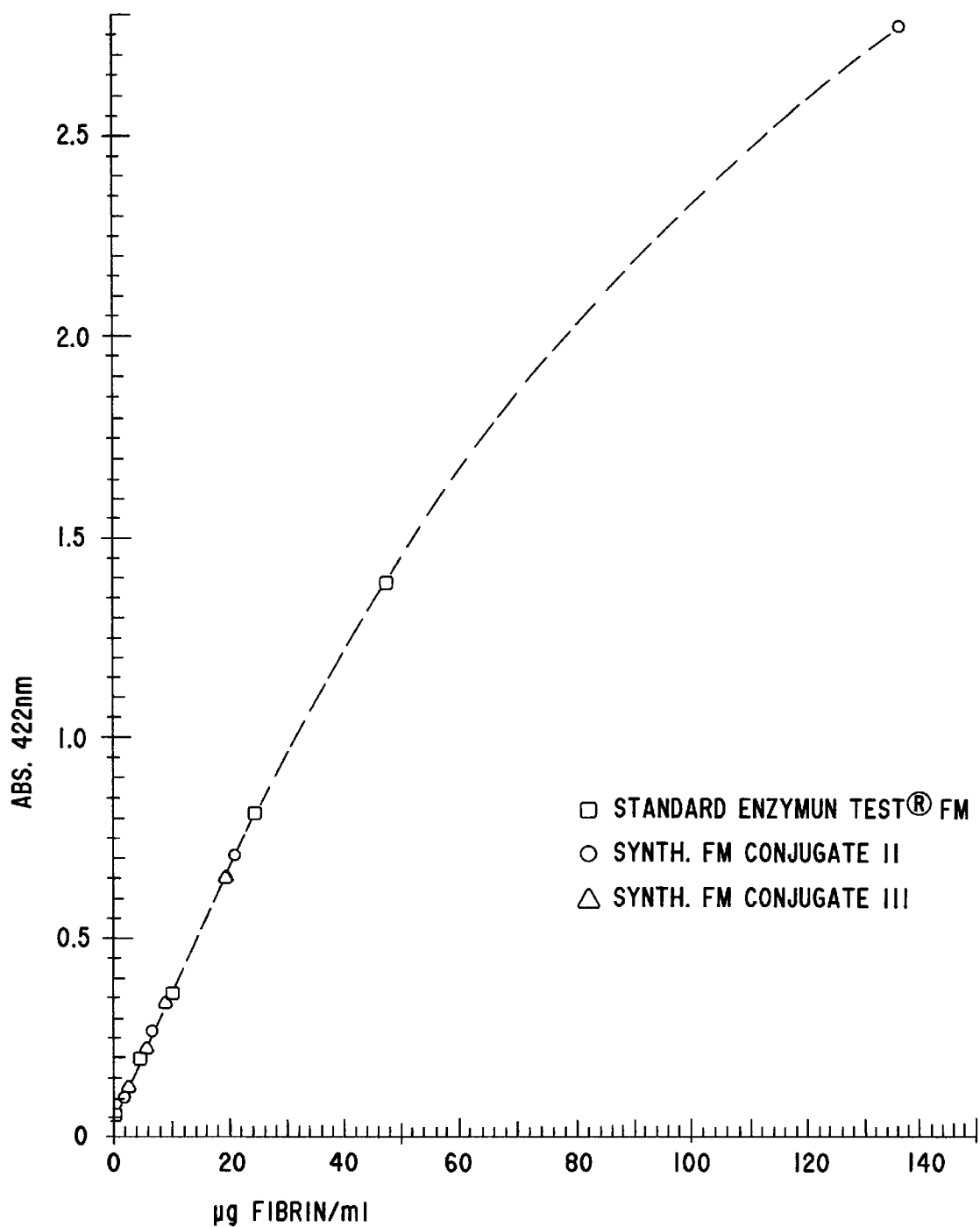
FIG. 4 shows the standard curves that were obtained according to example 10 using the synthetic FM conjugates II and III and a fibrin standard of the state of the art.

FIG. 4 shows the standard curves that were obtained according to example 10 using the synthetic FM conjugates II and III and a fibrin standard of the state of the art.

EXAMPLES

Example 1

Production of the synthetic troponin T conjugate Nα, Nε-Bis-(leucyl-lysyl-aspartyl-arginyl-isoleucyl-glutamyl-lysyl-arginyl-arginyl-alanyl-glutamyl-arginyl-alanyl-glutamyl-glutaminyl-glutaminyl-arginyl-isoleucyl- arginyl-asparagyl-glutamyl-arginyl-glutamyl-lysyl- glutamyl-arginyl-glutaminyl-B-alanyl-B-alanyl)- lysinamide (I)

The conjugate (I) was produced by means of Fmoc-(fluorenylmethoxy-carbonyl-)-solid phase peptide synthesis using a SMPS 350 peptide synthesizer from the ZINSSER Analytic Company on 15 mg 4-(2',4'-dimethoxy-phenyl-Fmoc-aminomethyl)-phenoxy resin SA5030 from the ADVANCED CHEMTECH Company with a loading of 0.22 mmol/g. 90 µmol of each of the following N-Fmoc amino acid derivatives together with 90 µmol 1-hydroxybenzotriazole in 270 µl dimethylformamide and 105 µl of a dimethylformamide solution of 90 µmol N,N-diisopropylcarbodiimide were coupled twice in succession to the solid phase-bound peptide to be synthesized: Nε-Fmoc-lysine, β-alanine, β-alanine, glutamine(-trityl), arginine(-pentamethylchromane), glutamic acid(-tert. butyl ester), Nε-tert. butyloxycarbonyl-lysine, glutamic acid-(-tert. butyl ester), arginine(-pentamethylchromane), glutamic acid(-tert. butyl ester), asparagine(-trityl), arginine(-pentamethylchromane), glutamic acid(-tert. butyl ester), alanine, arginine (-pentamethylchromane, arginine(-pentamethylchromane), Nε-tert. butyloxycarbonyl-lysine, glutamic acid(-tert. butyl ester), isoleucine, arginine(-pentamethylchromane), aspartic acid(-tert. butyl ester), Nε-tert. butyloxycarbonyl-lysine, leucine. The coupling times are 40 and 30 minutes. The cleavage time of the Fmoc protecting group is carried out after each double coupling using 600 µl of a 50% solution of piperidine in dimethyl-formamide. The cleavage time is 20 minutes. The washing steps are carried out eight times after each of the reaction steps with 700 µl dimethyl-formamide each time. The peptide is released by treating the resin filtered free of solvent with 750 µl in each case of a mixture of 90% trifluoroacetic acid, 3% thioanisole, 3% ethanedithiol and 3% thiocresol within 20 minutes and subsequently for 140 minutes. The product is precipitated by addition of 15 ml cold diisopropyl ether to the pooled filtrate and isolated by filtration. The residue is dissolved in 3 ml 50% acetic acid and lyophilized. The lyophilisation procedure is repeated twice. 10 mg crude material with a purity of 48% according to reverse-phase HPLC is obtained of which 5 mg is purified by means of preparative reverse-phase HPLC. Yield 1 mg (LSIMS liquid single ion monitoring mass spectrometry: M-H+: 7438.4; matrix; mNBA meta-nitrobenzoic acid, accelerator voltage: 6 kV).

Example 2

Production of the synthetic troponin T conjugate leucyl-lysyl-aspartyl-arginyl-isoleucyl-glutamyl-lysyl-arginyl-arginyl-alanyl-glutamyl-arginyl-alanyl-glutamyl-glutaminyl-glutaminyl-arginyl-isoleucyl- arginyl- aspargyl-glutamyl-arginyl-glutamyl-lysyl-glutamyl- arginyl-glutaminyl-leucyl-lysyl-aspartyl-arginyl- isoleucyl-glutamyl-lysyl-arginyl-arginyl-alanyl- glutamyl-arginyl-alanyl-glutamyl-glutaminyl-glutaminyl- arginyl-isoleucyl-arginyl-aspargyl-glutamyl-arginyl- glutamyl-lysyl-glutamyl-arginyl-glutamine (II).

The conjugate (II) was produced by means of Fmoc-(fluorenylmethoxy-carbonyl-)-solid phase peptide synthesis using a SMPS 350 peptide synthesizer from the ZINSSER Analytic Company on 15 mg 4-(2',4'-dimethoxy-phenyl-Fmoc-aminomethyl)-phenoxy resin SA5030 from the ADVANCED CHEMTECH Company with a loading of 0.22 mmol/g. 90 µmol of each of the following N-Fmoc amino acid derivatives together with 90 µmol 1-hydroxybenzotriazole in 270 µl DMF (dimethylformamide) and 105 µl of a DMF solution of 90 µmol N,N-diisopropylcarbodiimide were coupled twice in succession to the solid-phase-bound peptide to be synthesized: glutamine(-trityl), arginine (pentamethylchromane), glutamic acid (tert. butyl ester), lysine (tert. butyloxycarbonyl), glutamic acid (tert. butyl ester), arginine (pentamethylchromane), glutamic acid (tert. butyl ester), asparagine (trityl), arginine (pentamethylchromane), isoleucine, arginine (pentamethylchromane), glutamine (trityl), glutamine (trityl), glutamic acid (tert. butyl ester), alanine, arginine (pentamethylchromane), glutamic acid (tert. butyl ester), alanine, arginine (pentamethylchromane), arginine (pentamethylchromane), lysine (tert. butyloxycarbonyl), glutamic acid (tert. butyl ester), isoleucine, arginine (pentamethylchromane), aspartic acid (tert. butyl ester), lysine (tert. butyloxycarbonyl), leucine. After coupling the leucine, the same amino acid sequence is again sequentially synthesized onto this. The coupling times are 40 and 30 minutes. The cleavage time of the Fmoc protecting group is carried out after each double coupling using 600 µl of a 50% solution of piperidine in DMF. The cleavage time is 20 minutes and is repeated once. The washing steps are carried out eight times after each of the reaction steps with 700 µl DMF each time. The peptide is released by treating the resin filtered free of solvent with 750 µl in each case of a mixture of 90% trifluoroacetic acid, 3% thioanisole, 3% ethanedithiol and 3% thiocresol within 20 minutes and subsequently for 140 minutes. The product is precipitated by addition of 15 ml cold diisopropyl ether to the pooled filtrate and isolated by filtration. The residue is dissolved in 3 ml 50% acetic acid and lyophilized. The lyophilisation procedure is repeated twice. 17 mg crude material with a purity of 52% according to reverse-phase HPLC is obtained of which 5 mg is purified by means of preparative reverse-phase HPLC. 1 mg pure material (according to HPLC >99%) is obtained.

Example 3

Determination of troponin T in an electro-chemiluminescence immunoassay

A biotin-labelled monoclonal antibody (MAB) against troponin T and a ruthenium-Tris(bispyridyl)-labelled antibody are incubated for 10 minutes with troponin T-coated and streptavidin-coated magnetic polymer particles (beads). During the incubation period the immunocomplex as well as the binding of the biotinylated MABs to the magnetic particles is formed. The reaction is ended by withdrawing the reaction mixture in the measuring cell by suction. The magnetic polymer particles are immobilized on the electrode in the measuring chamber by a magnet. The remaining reaction mixture is removed by suction and the magnetic particles are washed with assay buffer. Subsequently the light emission is excited by applying an electrical voltage.

Reagents:
Solution 1:
Incubation buffer:
100 mM sodium phosphate pH 7.0
0.1% BSA (bovine serum albumin)
0.1% methylisothiazolone
0.1% sodium benzoate Solution 2:
Biotinylated MAB against troponin T, 2 µg/ml in incubation buffer.

Solution 3:
Ruthenium-Tris(bispyridyl)-labelled MAB against troponin T, 2 μg/ml in incubation buffer Solution 4:
600 μg/ml magnetic beads, streptavidin-coated in: 50 mM Hepes buffer, 0.1% BSA, 0.1% Thesit, 0.1% chloroacetamide, 0.01% methylisothiazolone, pH 7.4

Solution 5:
Assay buffer: pH 6.8
0.16M Tris-propylamine, 0.2M di-potassium hydrogen phosphate, 0.1% polydocanol (Thesit), 0.1% Oxaban A The conjugates to be tested are weighed in human serum or incubation buffer. The signal which one obtains by measuring these samples in methods described above is compared with the signal which is obtained with the calibration solutions. The quotient recovery/weighed-in quantity is calculated from this.

60 μl of each of the solutions 1–4 is incubated with 60 μl sample for 10 minutes at room temperature. Afterwards the reaction mixture in the measuring chamber is removed by suction and the magnetic particles are separated. The measuring chamber is filled with assay buffer and the measured signal is recorded. The concentration of the samples is determined by comparing the signal with that of the calibration solutions.

The measurement was carried out on an Origen 1.0 instrument from the Igen Company USA.

The results are shown in Table 1.

TABLE 1

|  | freshly weighed | Recovery[2] after 3 weeks −20° C. | after 3 weeks 4° C. |
| --- | --- | --- | --- |
| a) Conjugate I |  |  |  |
| Std a | 218144[1] | 95% | 93% |
| Std b | 320998 | 88% | 102% |
| Std c | 620489 | 94% | 95% |
| Std d | 2416923 | 92% | 90% |
| Std e | 4275586 | 90% | 88% |
| b) Conjugate II |  |  |  |
| Std a | 318143[1] | 90% | 90% |
| Std b | 4420798 | 88% | 100% |
| Std c | 720789 | 90% | 92% |
| Std d | 2616522 | 93% | 85% |
| Std e | 4576789 | 88% | 83% |
| c) Human heart troponin T |  |  |  |
| Std a | 241233[1] | 95% | 60% |
| Std b | 467345 | 98% | 58% |
| Std c | 814325 | 93% | 55% |
| Std d | 2456342 | 88% | 63% |
| Std e | 4675432 | 89% | 59% |

[1]light emission units
[2]recovery in % of the measured result that is obtained immediately after preparation of the solutions. Storage at 35° C.
[3]Std: troponin standard (previously the conventional standard from the Enzymun test TnT, Boehringer Mannheim GmbH)

Example 4
Production of the troponin T conjugate (III)

200 mg bovine serum albumin (2.9 μmol) is dissolved in 6 ml 0.1M potassium phosphate buffer pH 8.0. 44.6 mg maleinimidohexanoic acid-N-hydroxysuccinimide ester (145 μmol) is dissolved in 0.5 ml dioxan and added dropwise to the above solution. It is allowed to stir for 17 hours at room temperature (RT).

The above solution is filtered over a column (3 cm×40 cm) filled with Aca 202 (Pharmacia) that has been equilibrated with 0.1M potassium phosphate buffer pH 6.0 (detection λ=226 nm). The first peak is collected and its protein content is determined according to the method of Pierce (BCA bicinchoninic acid method). The loading of maleinimidohexanoyl groups obtained is determined according to the method of Ellman. It is 17.5 maleinimidohexanoyl groups per molecule bovine serum albumin.

10 mg cysteinyl-β-alanyl-β-alanyl-alanyl-glutamyl-glutaminyl-glutaminyl-arginyl-soeucyl-arginyl-asparaginyl-glutamyl-arginyl-glutamyl-lysyl-glutamyl-arginyl-amide (4.79 μmol) and 8.2 g cysteinyl-γ-aminocaproyl-seryl-leucyl-lysyl-aspartyl-arginyl-isoleucyl-glutamyl-lysyl-arginyl-arginyl-alanyl- glutamyl-amide (4.79 μmol) are dissolved in 1 ml 0.1M potassium phosphate buffer pH 6.0. The solution is saturated with argon. 2.13 ml of a solution of maleinimidohexanoyl-activated bovine serum albumin (loading 17.5:1) at a concentration of 9.46 mg/ml in 0.1M potassium phosphate buffer pH 6.0 is added to the above solution. It is again saturated with argon and stirred at room temperature for 17 hours while excluding oxygen. 4 ml 0.05M succinic acid buffer pH 4.0 is added and it is dialysed 4 times against 1 liter 1% acetic acid. The insoluble precipitate is centrifuged.

The above solution is filtered over a column (3 cm×28 cm) filled with Aca 202 (Pharmacia) which has been equilibrated with 0.05M succinic acid buffer pH 4.0 (detection λ=226 nm). The first peak is collected and its protein content is determined according to the method of Pierce (BCA method). 19.8 mg protein conjugate in 35 ml solution is found. No further maleinimido activity is detected by the method of Ellman.

Example 5
Production of the troponin T conjugate (IV)

200 mg bovine serum albumin (2.9 μmol) is dissolved in 6 ml 0.1M potassium phosphate buffer pH 8.0. 44.6 mg maleinimidohexanoic acid-N-hydroxysuccinimide ester (145 μmol) is dissolved in 0.5 ml dioxan and added to the above solution. It is allowed to stir for 17 hours at room temperature.

The above solution is filtered over a column (3 cm×40 cm) filled with Aca 202 (Pharmacia) that has been equilibrated with 0.1M potassium phosphate buffer pH 6.0 (detection λ=226 nm). The first peak is collected and its protein content is determined according to the method of Pierce (BCA method). The loading of maleinimidohexanoyl groups obtained is determined according to the method of Ellman as 18.0 per molecule bovine serum albumin. 35 mg cysteinyl-γ-aminocaproyl-leucyl-lysyl-aspartyl- arginyl-isoleucyl-glutamyl-lysyl-arginyl-arginyl-alanyl- glutamyl-arginyl-alanyl-glutamyl-glutaminyl-glutaminyl- arginyl-isoleucyl-arginyl-aspargyl-glutamyl-arginyl- glutamyl-lysyl-glutamyl-arginyl-glutamyl-amide (9.6 μmol) is dissolved in 3 ml 0.1M potassium phosphate buffer pH 6.0 and the solution is saturated with argon. 2.35 ml of the maleinimidohexanoyl-activated bovine serum albumin solution (c=9.2 mg/ml) is added to the peptide solution and this entire solution is again saturated with argon. The solution is stirred at room temperature for 17 hours. After addition of 0.5 ml 50% acetic acid, it is filtered over a G4 glass filter frit. The eluate is filtered over a column (3 cm×40 cm) filled with Aca 202 (Pharmacia) which has been equilibrated with 0.1M potassium phosphate buffer pH 6.0 (detection λ=226 nm). The first peak is collected and its protein content is determined according to the method of Pierce (BCA method). 25 mg protein conjugate in 25.5 ml eluate is found. No further maleinimido activity is detected by the method of Ellman.

Example 6

Stabilities of the synthetic troponin T calibrator (I)

The stability of the troponin T conjugate (I) according to example 1 was compared with the stability of a calibrator made from native antigen. Troponin T from bovine heart (bcTnT) and human heart (hcTnT) was used as the native antigen.

The calibrators were stored for up to three weeks at temperatures of −80° C., 4° C. and 25° C. The measured signal obtained with this calibrator was determined at weekly intervals and compared with the initial signal. The test procedure corresponds to example 3.

There were no differences when stored at −80° C. All calibrators still showed a 100% stability after 3 weeks. Storage at 4° C. also yielded no significant differences. Only in the case of bcTnT did the measured signal fall to 92% of the initial signal after 3 weeks.

The superior stability of the calibrator according to the invention was apparent when stored at 25° C. Whereas the measured signal in the case of hcTnT and bcTnT fell to 24 and 5% respectively of the initial signal after 3 weeks at 25° C., the signal of the synthetic calibrator was still 50% of the initial value.

Example 7

Production of the synthetic FM conjugate (I) for a test for soluble fibrin.

The FM conjugate (I) for the test for soluble fibrin was synthesized by means of Fmoc- (fluorenylmethoxycarbonyl-) solid phase peptide synthesis using a SMPS 350 peptide synthesizer from the ZINSSER Analytic Company on 15 mg 4-(2',4'-dimethoxyphenyl-Fmoc-aminomethyl)-phenoxy resin SA 5030 from the ADVANCED CHEMTECH Company with a loading of 0.22 mmol/g. 90 µmol of each of the following N-Fmoc-amino acid derivatives together with 90 µmol 1-hydroxybenzotriazole in 270 µl dimethylformamide and 105 µl of dimethylformamide solution of 90 µmol N,N-diisopropylcarbodiimide were coupled twice in succession to the solid-phase-bound peptide to be synthesized: Nε-Fmoc-lysine, β-alanine, β-alanine, arginine(-pentamethylchromane), glutamic acid(-tert. butyl ester), valine, valine, arginine (-pentamethylchromane), proline and glycine. The coupling times are 40 and 30 minutes. The cleavage time of the Fmoc protecting group is carried out after each double coupling with 600 µl of a 50% solution of piperidine in dimethylformamide. The washing steps are carried out eight times after each of the reaction steps with 700 µl dimethylformamide each time. The peptide is released by treating the resin filtered free of solvent with 750 µl in each case of a mixture of 90% trifluoroacetic acid, 3% thioanisole, 3% ethanedithiol and 3% thiocresol within 20 minutes and subsequently for 140 minutes. The product is precipitated by addition of 15 ml cold diisopropyl ether to the pooled filtrate and isolated by filtration. The residue is dissolved in 3 ml 50% acetic acid and lyophilized. The lyophilisation procedure is repeated twice. 7 mg crude material of a purity of 53% according to reverse-phase HPLC is obtained of which 5 mg is purified by means of preparative reverse-phase HPLC. Yield: 1.25 mg (LSIMS: M-H$^+$: 2300.5; matrix; mNBA, accelerator voltage: 6 kV).

In this way a conjugate is formed of two peptides corresponding to the sequence shown in SEQ ID NO. 11 which are each linked to lysine via a spacer composed in each case of two molecules of β-alanine.

Example 8

Production of the synthetic FM conjugate (II) for a test for soluble fibrin

The FM conjugate (II) for the test for soluble fibrin was synthesized by means of Fmoc- (fluorenylmethoxycarbonyl-) solid phase peptide synthesis using a SMPS 350 peptide synthesizer from the ZINSSER Analytic Company on 15 mg 4-(2',4'-dimethoxyphenyl-Fmoc-aminomethyl)-phenoxy resin SA 5030 from the ADVANCED CHEMTECH Company with a loading of 0.22 mmol/g. 90 µmol of each of the following N-Fmoc-amino acid derivatives together with 90 µmol 1-hydroxybenzotriazole in 270 µl dimethylformamide and 105 µl of a dimethylformamide solution of 90 µmol N,N-diisopropylcarbodiimide were coupled twice in succession to the solid-phase-bound peptide to be synthesized: Nε-Fmoc-lysine, Nε-Fmoc-lysine, β-alanine, β-alanine, arginine(-pentamethylchromane), glutamic acid (-tert. butyl ester), valine, valine, argine(-pentamethylchromane), proline and glycine. The coupling times are 40 and 30 minutes. The cleavage time of the Fmoc protecting group is carried out after each double coupling using 600 µl of a 50% solution of piperidine in dimethylformamide. The washing steps are carried out eight times after each of the reaction steps with 700 µl dimethylformamide each time. The peptide is released by treating the resin filtered free of solvent with 750 µl in each case of a mixture of 90% trifluoroacetic acid, 3% thioanisole, 3% ethane-dithiol and 3% thiocresol within 20 minutes and subsequently for 140 minutes. The product is precipitated by addition of 15 ml cold diisopropyl ether to the pooled filtrate and isolated by filtration. The residue is dissolved in 3 ml 50% acetic acid and lyophilized. The lyophilisation procedure is repeated twice. 15 mg crude material of a purity of 48% according to reverse-phase HPLC is obtained of which 5 mg is purified by means of preparative reverse-phase HPLC. Yield: 1.02 mg (LSIMS: M-H$^+$: 4854.3; matrix; mNBA, accelerator voltage: 6 kV).

In this way a conjugate is formed of four peptides corresponding to the sequence shown in SEQ ID NO. 11 which are each linked via a spacer of two molecules to a carrier composed of 3 lysine residues (FIG. 3a).

Example 9

Production of the synthetic FM conjugate (III) for soluble fibrin

The FM conjugate (III) for a test for soluble fibrin was synthesized by means of Fmoc- (fluorenylmethoxycarbonyl-) solid phase peptide synthesis using a SMPS 350 peptide synthesizer from the ZINSSER Analytic Company on 15 mg 4-(2',4'-dimethoxyphenyl-Fmoc-aminomethyl)-phenoxy resin SA 5030 from the ADVANCED CHEMTECH Company with a loading of 0.22 mmol/g. 90 µmol of each of the following N-Fmoc-amino acid derivatives together with 90 µmol 1-hydroxybenzotriazole in 270 µl dimethylformamide and 105 µl of a dimethylformamide solution of 90 µmol N,N-diisopropylcarbodiimide were coupled twice in succession to the solid phase-bound peptide to be synthesized: Nε-Fmoc-lysine, Nε-Fmoc-lysine, Nε-Fmoc-lysine, β-alanine, β-alanine, arginine (-pentamethylchromane), glutamic acid (-tert. butyl ester), valine, valine, arginine(-pentamethylchromane), proline and glycine. The coupling times are 40 and 30 minutes. The cleavage time of the Fmoc protecting group is carried out after each double coupling using 600 µl of a 50% solution of piperidine in dimethylformamide. The washing steps are carried out eight times after each of the reaction steps with 700 µl dimethylformamide each time. The peptide is released by treating the resin filtered free of solvent with 750 µl in each case of a mixture of 90% trifluoroacetic acid, 3% thioanisole, 3% ethanedithiol and 3% thiocresol within 20 minutes and subsequently for 140 minutes. The product is precipitated by addition of 15 ml cold diisopropyl ether to the pooled filtrate and isolated by filtration. The residue is dissolved in 3 ml 50% acetic acid and lyophilized. The lyophilisation procedure is repeated twice. 23 mg crude material of a purity of 42% according to reverse-phase HPLC is obtained of which 5 mg is purified by means of preparative reverse-phase HPLC. Yield: 0.95 mg.

In this way a conjugate is formed of eight peptides corresponding to the sequence shown in SEQ ID NO. 11 which are each linked via a spacer of two β-alanine molecules to a carrier composed of 7 lysine residues (FIG. 3b).

Example 10

Comparison of a fibrin standard with the synthetic FM conjugates I, II and III in a test for soluble fibrin The production of fibrin, the fibrin standard and fibrin degradation products as well as the treatment of the sample were carried out according to Lill et al., Blood Coagulation and Fibrinolysis 4 (1993) 97–102.

Test Principle

A two-step sandwich assay was carried out using streptavidin-coated tubes as the solid phase. The same fibrin-specific monoclonal antibody was used as the biotinylated capture MAB and as the peroxidase-labelled MAB.

The test was carried out at room temperature on an ES 33 instrument.

20 µl plasma was incubated with 60 µl incubation buffer (5.33M KSCN, 0.025M sodium phosphate, pH 7.3) for 30 minutes in streptavidin-coated polystyrene tubes (Boehringer Mannheim GmbH). 1000 µl biotinylated antibody solution (1.3 µg/ml biotinylated antibody, 0.1M potassium phosphate, 5.9 mg/ml bovine serum albumin, 0.5 mg/ml Tween 20®, pH 7.0) was added and it was incubated for 30 minutes. The antibody was obtained by immunizing Balb/c mice with the synthetic N-terminal heptapeptide Gly-Pro-Arg-Val-Val-Glu-Arg from the α-group of fibrin. The peptide was coupled by means of maleinimidobenzoyl-N-hydroxysuccinimide ester to Keyhole limpet haemocyanin. The monoclonal antibodies were obtained according to Köhler and Milstein, Nature 256 (1975), 495–497. The tube was subsequently washed with 4.3 mM NaCl solution. Afterwards 1000 µl peroxidase-labelled antibody solution (0.14 U/ml peroxidase conjugate, 0.035M potassium phosphate, 0.154M NaCl, 10 mg/ml polyethylene glycol 40000, 2 mg/ml bovine serum albumin, 0.5 mg/ml Tween 20®, pH 7.4) was added and it was incubated for 30 minutes. Afterwards the solution was removed from the tube and this was washed with 4.3 mM NaCl solution.

1000 µl ABTS® solution (Boehringer Mannheim GmbH) was added and it was incubated for 30 minutes. The absorbance was subsequently measured at 422 nm wavelength and the fibrin concentration was determined by comparison with the standard curve.

Standard Curves

FIG. 4 shows standard curves. These were determined in the range of 0 to 50 µg/ml fibrin. The fibrin standard of the Enzymun Test FM (Boehringer Mannheim GmbH) and the synthetic FM conjugates II and III were used as standards. Lyophilised plasma samples which were supplemented with the FM conjugates served as standards.

The results are shown in FIG. 4. It shows a very high correlation between the conjugates according to the invention and the standard of the state of the art.

We claim:

1. A peptidic calibrator for preparation of a calibration curve in a sandwich immunoassay for detecting an antigen wherein the immunoassays uses at least a first receptor and a second receptor which do not compete for the same binding site of the antigen, wherein the peptidic calibrator comprises a conjugate of
    (i) at least two peptides which specifically bind to the first receptor and
    (ii) at least two peptides which specifically bind to the second receptor, wherein the peptides of the calibrator are linked by at least one water soluble carrier polymer, wherein said antigen is selected from the group consisting of troponin T and a fibrin monomer, and wherein the peptides in the calibrator are products of synthetic or recombinant production.

2. The peptidic calibrator according to claim 1, wherein each peptide of the calibrator is selected from the group consisting of (i) said peptide, (ii) a derivative of said peptide in which at least one amino acid has been derivatized by a chemical reaction or substituted by another amino acid such that the derivative specifically binds to its respective receptor, and (iii) a mimetic of said peptide.

3. The peptidic calibrator according to claim 2, wherein said peptide has a backbone length of at least four amino acids.

4. The peptidic calibrator according to claim 3, wherein said peptide has a backbone length of 4–20 amino acids.

5. The peptidic calibrator according to claim 1, wherein said calibrator is a lyophilisate.

6. The peptidic calibrator according to claim 1, wherein said calibrator is in a liquid.

7. The peptidic calibrator according to claim 1, wherein the calibrator comprises 2–50 molecules of each peptide.

8. The peptidic calibrator according to claim 1, wherein the carrier polymer is composed of a plurality of oligomers.

9. The peptidic calibrator according to claim 1, wherein the carrier polymer comprises a branching point comprising a bi-functional or multi-functional molecule to which the peptides or further branching points are linked.

10. The peptidic calibrator according to claim 9, wherein the branching point is a bisamino acid.

11. The peptidic calibrator according to claim 9, wherein the peptides are linked to the branching point via a spacer.

12. The peptidic calibrator according to claim 11, wherein the spacer has a length of 3–40 atoms.

13. The peptidic calibrator according to claim 1, wherein the peptides comprise at least two different peptides selected from the group consisting of the amino acids shown in SEQ ID NOS: 1–10.

14. The peptidic calibrator of claim 1, wherein the calibrator comprises a conjugate of two peptides which specifically bind to the first receptor and two peptides which specifically bind to the second receptor.

15. The peptidic calibrator according to claim 1, wherein the carrier polymer has a molecular weight between 1000 and 5 million Daltons.

16. An immunoassay method for determining an antigen in a sample comprising contacting the sample with at least a first receptor and a second receptor which specifically bind the antigen and do not compete for the same binding site of the antigen to form a complex and detecting the complex formed as a measure of the amount of the antigen in the sample, said immunoassay comprising:

a) contacting a known amount of a peptidic calibrator correlative of a known concentration of said antigen to said at least first and second receptors in said immunoassay, wherein said peptidic calibrator comprises a conjugate of
(i) at least two peptides which specifically bind to the first receptor and
(ii) at least two peptides which specifically bind to the second receptor, wherein the peptides which bind to the first and second receptors are linked by at least one water soluble carrier polymers wherein the peptides are products of synthetic or recombinant production, and wherein each peptide has a sequence which is bound by the binding site of either the first or second receptors, said sequence being part of said antigen's sequence, b) measuring any complex formed between said peptidic calibrator and said first and second receptors, c) preparing a calibration curve with the measurement from step b), d) in a separate reaction, contacting said sample with said first and second receptors, e) measuring any complex formed between said antigen and said first and second receptors in step d), and f) determining the antigen concentration in the sample by comparing the measurement obtained in step e) with the calibration curve obtained from step c).

17. A method of preparing a calibration curve for an immunoassay for determining an antigen which is specifically bound by at least a first receptor and a second receptor wherein the receptors do not compete for the same binding site of the antigen, comprising the steps of a) contacting a known amount of a peptidic calibrator correlative of known concentration of said antigen to at least said first and second receptors in said immunoassay, wherein said peptidic calibrator comprises a conjugate of
(i) at least two peptides which specifically bind to the first receptor and
(ii) at least two peptides which specifically bind to the second receptor, wherein the peptides which bind to the first and second receptors are linked by at least one water soluble carrier polymers the peptides are products of synthetic or recombinant production, and wherein each peptide has a sequence which is bound by the binding site of either the first or second receptors, said sequence being part of said antigen's sequence, b) measuring any complex formed between said peptidic calibrator and said first and second receptors, and c) preparing a calibration curve using the measurement from step b).

18. The method according to claim 17, wherein the antigen is troponin T.

19. The method according to claim 17, wherein the antigen is a fibrin monomer.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Leu Lys Asp Arg Ile Glu Lys Arg Arg Ala Glu
1               5                   1 0

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu Ile Glu Ala His Phe Glu Asn 1               5

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Leu Gln Ala Leu Ile Glu Ala His Phe Glu Asn
1               5                   10

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Leu Asn Glu Leu Gln Ala Leu Ile Glu Ala His Phe Glu Asn
1               5                   10

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Pro Pro Lys Ile Pro Asp Gly Glu Arg
1               5

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Glu Gln Gln Arg Ile Arg Asn Glu Arg Glu Lys Glu
1               5                   10

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ala Leu Ser Asn Met Met His Phe

-continued (2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met  Pro  Asn  Leu  Val  Pro  Pro  Lys  Ile
1                   5
```

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Leu  Gln  Glu  Lys  Phe  Lys  Gln  Gln  Lys  Tyr
1                   5                        10
```

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Val  Leu  Arg  Asn  Arg  Ile  Asn  Asp  Asn  Gln
1                   5                        10
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gly  Pro  Arg  Val  Val  Glu  Arg
1                   5
```